(12) United States Patent
Franzen

(10) Patent No.: US 6,750,022 B2
(45) Date of Patent: Jun. 15, 2004

(54) MUTATION ANALYSIS BY PCR AND MASS SPECTROMETRY

(75) Inventor: Jochen Franzen, Bremen (DE)

(73) Assignee: Bruker Daltonik GmbH (DE)

( * ) Notice: Subject to any disclaimer, the term of this patent is extended or adjusted under 35 U.S.C. 154(b) by 0 days.

(21) Appl. No.: 10/079,271

(22) Filed: Feb. 20, 2002

(65) Prior Publication Data

US 2003/0148293 A1 Aug. 7, 2003

(30) Foreign Application Priority Data

Feb. 1, 2002 (EP) ............................................ 02002522

(51) Int. Cl.⁷ .......................... C12Q 1/68; C12N 15/00; C12N 15/63; C12N 1/20; C07H 21/04
(52) U.S. Cl. ..................... 435/6; 435/320.1; 435/252.8; 435/174; 435/183; 382/129; 382/133; 382/153; 382/173; 382/286; 382/291; 702/19; 702/22; 935/10; 935/24; 935/72; 536/22.1
(58) Field of Search ..................... 435/6, 70.1, 320.1, 435/91.1, 91.2; 530/350; 536/23.4; 935/6; 436/518

(56) References Cited

U.S. PATENT DOCUMENTS

| 5,830,655 | A | 11/1998 | Monforte et al. | |
|---|---|---|---|---|
| 5,869,242 | A | 2/1999 | Kamb | |
| 6,258,538 | B1 | 7/2001 | Köster et al. | |
| 6,391,548 | B1 | * | 5/2002 | Bauer ........................... 435/6 |
| 6,544,745 | B2 | * | 4/2003 | Davis ........................... 435/6 |

FOREIGN PATENT DOCUMENTS

| EP | 1 138 782 A | 10/2001 | |
|---|---|---|---|
| WO | WO 96/27681 | 9/1996 | |
| WO | WO 96/3763 | 11/1996 | |
| WO | WO 97/27325 | * 7/1997 | ................... 435/6 |
| WO | WO 97 33000 A | 9/1997 | |
| WO | WO 98 54571 A | 12/1998 | |

OTHER PUBLICATIONS

Sauer et al., "A novel procedure for efficent genotyping of single nucleotide polymorphisms", Nucleic Acids research, (2000), vol. 28, No. 5, pp. e13 i–viii.*
Phillip Ordoukhanian and John–Stephen Taylor, Design and Synthesis of a Versatile Photocleavable DNA Building Block. Application to Phototriggered Hybridization, American Chemical Society 1995, vol. 117, pp. 9570–9571, St. Louis, Missouri.
Jeffrey W. Walker, Gordon P. Reid, James A. McCray, and David R. Trentham, Photolabile 1–(2–Nitrophenyl)ethyl Phosphate Esters of Adenine Nucleotide Analogues. Synthesis and Mechanism of Photolysis, American Chemical Society 1988, vol. 110, pp. 7170–7177, London, United Kingdom.
Laken, Steven J., et al., Genotyping by mass spectrometric analysis of short DNA fragments, Nature Biotechnology, Nature Publising,vol. 16, pp. 1352–1356, Dec. 1998, Lyon, France.

* cited by examiner

Primary Examiner—Jeffrey Fredman
Assistant Examiner—Arun Chakrabarti

(57) ABSTRACT

The invention concerns mass spectrometric analysis of known mutation sites in the genome, such as single nucleotide polymorphisms (SNPs). The invention uses minor amounts of primers with photocleavable linkers, intermixed with a major amounts of primers without linkers, to produce short mutation-containing DNA sequences by enzymatic amplification procedures such as polymerase chain reactions (PCR). After this single amplification procedure, the linker-containing PCR by-products are extracted, washed and photolytically cleaved. Short oligonucleotides are produced which facilitate mass spectrometric analysis. Additionally to the use of linkers, some types of primers may contain blockers which stop the polymerase copying process to achieve even shorter oligonucleotides for analysis.

14 Claims, 3 Drawing Sheets

```
(2a) ...NNNNNNNNNNNNNNNNNNNNNNNNNNNNNNNNNNNNPNNNNNNNNNNNNNNNNNNNNNNNNNNNNNNNNN...
(2b) ...MMMMMMMMMMMMMMMMMMMMMMMMMMMMMMMMMMQMMMMMMMMMMMMMMMMMMMMMMMMMMMMMMMMM...

(2c)         111111111111111-

(2d)                                        -222222222222222

(2e)         111111111111111MMMMMMMMMMMQMMMMMMMMMMMMMMMMMMMMMMMMMM (2f)         NNNNNNNNNNNNNNNNNNNNNNNNNNNNPNNNNNNNNNNNNN222222222222222

(2g)                   A3333333L3333-
(2h)                   A3333333L3333MQMMMMMMMMMMMMMMMMMMMMMMMMMMM (2i)                                  -4444L44444444A
(2j)         NNNNNNNNNNNNNNNNNNNNNNNNNNNNNP4444L44444444A (2k)                   A3333333L3333MQMMMM
(2l)                                  NNNNNP4444L44444444A (2m)                              +3333MQMMMMMMMMMMMMMMMMMMMMMMMMM
(2n)                              +3333MQMMMM
(2o)         NNNNNNNNNNNNNNNNNNNNNNNNNNNNNP4444+
(2p)                                  NNNNNP4444+
```

Figure 2

```
(3a) ...NNNNNNNNNNNNNNNNNNNNNNNNNNNNNNNNNNNNPNNNNNNNNNNNNNNNNNNNNNNNNNNNNNNNNN...
(3b) ...MMMMMMMMMMMMMMMMMMMMMMMMMMMMMMMMMMQMMMMMMMMMMMMMMMMMMMMMMMMMMMMMMMMM...

(3c)         111111111111111-

(3d)                                        -222222222222222

(3e)         111111111111111MMMMMMMMMMMQMMMMMMMMMMMMMMMMMMMMMMMMMM (3f)         NNNNNNNNNNNNNNNNNNNNNNNNNNNNPNNNNNNNNNNNNN222222222222222

(3g)                   33333333333B-

(3h)                   33333333333BQMMMMMMMMMMMMMMMMMMMMMMMMMM (3i)                                  -4444L44444444A (3j)         NNNNNNNNNNNNNNNNNNNNNNNNNNNNNP4444L44444444A (3k)                              P4444L44444444A (3l)         NNNNNNNNNNNNNNNNNNNNNNNNNNNNNP4444+

MUTATION ANALYSIS BY PCR AND MASS SPECTROMETRY

FIELD OF THE INVENTION

The invention concerns mass spectrometric analysis of known mutation sites in the genome, such as single nucleotide polymorphisms (SNPs).

BACKGROUND OF THE INVENTION

Subject of this invention is a diagnostic method for the detection of actual mutative states in the genome DNA, whereby the possible mutation site has to be known beforehand. These mutative sequence changes, compared to the standardized sequence of a "wild type", may either be a base exchange ("point mutation") or the introduction of nucleotides ("insertion") or removal of nucleotides ("deletion"). Point mutations with a frequency above one percent in a population have been named "single nucleotide polymorphisms"; the abbreviation SNP has become particularly wide-spread in the recent literature. For humans, it is supposed that there are about 10 million SNPs which characterize most of the individually inherited differences between humans. They control the individual phenotypes. Roughly three million SNPs are estimated to be in the frequency range of 30 to 70 percent of the population. End of the year 2001, more than one and a quarter million SNPs were discovered and listed in the public data base NBCI of the worlwide acting SNP Consortium.

For the genome of a species, it is customary to define a "wild type" which is regarded as free of mutation, and a "mutant" which contains a mutation. Considering the frequency of mutations such as SNPs, and the equal value of mutants and wild types, the definition of the wild type is arbitrary or at least purely accidental, as already reflected in the term "polymorphism".

Nearly all DNA mutations, including all those defined above, produce differences in the mass of the DNA segment containing the mutation in comparison to the mass of a corresponding segment of the wild type. The precise mass determination of a DNA segment can therefore be used for the determination of a mutation. Exceptions of this rule are the relatively rare "rotations", an interchange of two bases in a sequence.

Mass spectrometry is a very powerful and precise tool for determining the mass of a bio-molecule. By using a mass spectrometric method, such as time-of-flight mass spectrometry (TOF-MS) with ionization by matrix-assisted laser desorption and ionization (MALDI), it is possible to analyze the ions for their masses. However, ionization can also be achieved using electrospray ionization (ESI), in the latter case with mass spectrometers which are frequently of a different type.

With polymerase chain reactions (PCR), using a pair of "selection primers", i.e. single strand oligonucleotides about 20 bases long, it is possible to produce amounts in the order of billions of double-strand PCR products with a length of at least 40 base pairs in a well-known way. The production process for these oligonucleotides increases the number of products exponentially by application of temperature cycles ("thermocycles"); such processes have become known under the general term "amplification". The mutation site can be incorporated in the products by adequately choosing the sequences of the two selection primers.

The obvious method to simply measure the mass of the PCR-amplified oligonucleotides as such by mass spectrometry, was found to be almost unworkable. The precise measurement of these DNA products with more than 40 base pairs proved itself to be almost impossible. The reasons for this are extremely low sensitivity for long DNA products because of difficult ionization, high probability of adduct formation with undefined numbers of sodium or potassium anions, and easy fragmentation of the fragile DNA products. These oligonucleotides have a poly-anionic character; each phosphate group of the DNA backbone forms an anion and has to be neutralized during ionization by a proton (which eagerly are replaced by alkali cations if present). A method therefore had to be found to provide as short oligonucleotides as possible, still containing the mutation site.

To this end, several methods of restricted, mutation-dependent primer extension using terminating derivatives of the nucleotide tri-phosphates have been developed in order to generate extended primers of approximately 12 to 25 nucleotides in length only, better suited to identify the nature of the mutation by mass spectrometry.

These methods basically consist of the following steps: Firstly, a sufficient number of copies of the DNA segment containing the mutation site is produced by PCR using a pair of selection primers. After extraction and washing, these DNA segments secondly serve as templates for the enzymatic, mutation-dependent extension of an "extension primer" by a second phase of thermocycling. In this second thermocycling phase, one to four of the nucleotide triphosphates are derivatized in such a manner that they serve as terminators for the extension, i.e., if the terminator is built in at the 3' end, a prolongation is no longer possible because the binding site is occupied. The extension primer may be identical with one of the two selection primers; however it is regularly much better to use an extension primer which is not identical.

The extension primer is a short DNA chain of approximately 10 to 20 nucleotides and functions as a recognition sequence for the site of a possible mutation. The extension primer is synthesized with a base sequence so that it can be "hybridized" or "annealed" to the template strand, being an exact compliment to the base sequence in the vicinity of a known point mutation site. (The attachment of a complementary strand is known as "hybridization" or "annealing").

Different types of primer extension procedures have been developed, generating either products with equal numbers of bases for mutants and wild types, differing only by the differences in weight of the different bases (9 to 40 atomic mass units as differences), or products with different numbers of bases (at least about 300 atomic mass units difference) for mutants and wild types. The latter are easier to measure by mass spectrometry, but somewhat more complicated to generate. In both cases, however, the PCR products of the first amplification cycle have to be cleaned from the nucleotide triphosphates and primers, new nucleotide triphosphates (including the terminating derivatives) and extension primers have to be added, and another set of copying thermocycles have to be applied. The final products, about 12 to 25 bases in length, again have to be thoroughly washed before mass spectrometric analysis. Primer extension procedures are complicated, using two different thermocycling and washing procedures subsequently, thus about doubling the effort of a pure PCR amplification.

The primer extension methods are widely covered by U.S. Pat. No. 6,258,538 ((H.Köster et al.).

All primer extension methods have to use rather expensive types of polymerases because not all polymerases can handle the terminating dNTP derivatives. The use of thermosequenase, especially developed for the Sanger method of sequencing, is highly recommended, more inexpensive polymerases do not correctly bind the terminators. Inexpensive polymerases, such as tac polymerase, can only be used in the first amplification by PCR.

Unfortunately, precise determination of the mass of even these relatively short primer extension oligonucleotides is still difficult. With a primer extension method delivering products with the same number of bases, the mass differences between wild type oligonucleotide and mutant oligonucleotide amount to 9 to 40 atomic mass units only. Because of the poly-anionic character of the DNA, various numbers of ubiquitous sodium (23 atomic mass units) or potassium ions (39 atomic mass units) are particularly likely to attach to the oligonucleotides (instead of protons), and so-called "adducts" are formed. The uncertainty in the degree to which the adducts are formed makes any precise mass determination exceptionally difficult-at the very least, it means that cleaning has to be extremely thorough to avoid the usually ubiquitous presence of any sodium or potassium cations and all relevant process parameters have to be carefully monitored for being kept constant.

Therefore, procedures have been searched for to shorten even more the relatively short primer extension products, including partial enzymatic digestion and chemical or enzymatic cleaving. These shortening procedures force to apply even more washing processes, even if the washing has not to be that thoroughful.

One of the methods to shorten the products which have to be analyzed mass spectrometrically was proposed by Monforte et al. (J. A. Monforte, C. H. Becker, T. A. Shaler, D. J. Pollart, WO 96/37630). The authors proposed the use of linkers which can be chemically or enzymatically cleaved. The necessary introduction of chemicals for the cleaving process, however, always has the disadvantage of introducing traces of impurities which again may form adducts. In addition, chemical cleavage needs adjustments of other parameters of the solution as for instance pH values, needing more chemicals to be added with the danger to introduce, e.g., alkali ions. Enzymatic cleaving, e.g. by restriction endonucleases, means a very restricted design of the primers which have to offer a recognition pattern for the nucleases and also needs adjusted buffer conditions for cleavage, making washing after cleavage a necessary step.

Another method of shortening the DNA products by partial digestion has been developed by Gut and Beck (WO 96/27681), together with a neutralization of the DNA products, generating more peptide-like products.

The MALDI preparation and measurement procedure consists of first embedding on a sample support the analyte molecules into small crystals of a solid UV-absorbent matrix, usually an organic acid. The sample support is introduced into the evacuated ion source of the mass spectrometer. The matrix is then evaporated by a short laser pulse of about 3 nanoseconds, producing a so-called plume consisting of a weakly ionized plasma which lasts for some tens of nanoseconds before it quickly expands into the surrounding vacuum. The evaporation process transports also the analyte molecules into the plasma plume. The analyte molecules are ionized as a result of collisions with matrix ions of the plume but, unfortunately, a condition-dependent and length-dependent percentage of the fragile DNA analyte molecules will be fragmented. The voltage which is applied to the ion source apertures accelerates the ions into the flight tube which has no electrical field. Due to their differing masses, the ions are accelerated to different velocities. The smaller ions reach the detector earlier than the larger ions. The flight times are measured and converted into ion masses.

MALDI is ideally suited for analyzing peptides and proteins. The analysis of nucleic acid chains is somewhat more difficult. Even in the case of short nucleic acid chains, ionization in the MALDI process is approximately 100 times less successful than it is for peptides; the sensitivity decreases superproportionally with increasing mass. The reason for this is that only a single proton has to be captured to ionize a peptide or a protein. For nucleic acids with multiple negative charges on the poly-anionic sugar-phosphate backbone (one negative charge for each nucleotide), the ionization process involving such a lot of protons is considerably less efficient. The DNA products which have to be detected must therefore be as short as possible so that they can be detected well.

In a similar way, an ionization method can also be used which uses a liquid with solved samples as the starting point. This is known as electrospray ionization (ESI). There are different types of mass spectrometers equipped with ESI ion sources, such as ion traps, FTMS, and time-of-flight mass spectrometers with orthogonal ion injection. The method is also ideally suited to the detection of peptides and proteins but has similar problems with oligonucleotides. Here also, the oligonucleotides which are to be detected have to be as short as possible.

SUMMARY OF THE INVENTION

The invention provides an easy procedure which produces sufficient amounts of ultrashort and ultraclean DNA products for mass spectrometric analysis; if any possible with only a single amplifying and a single washing process, thus reducing time, cost, and effort of sample preparation, compared to hitherto used methods of primer extension. The invention is based upon a single application of a cyclic enzymatic amplification process such as the polymerase chain reaction (PCR), however using in this process a mixture of primers without and with built-in photocleavable "linkers" with specified properties. The linker-containing primers cause the generation of short by-products during the amplification process which cannot be amplified further. After amplification, the short by-products are extracted, e.g. by affinity bonding to substrates, washed, and cleaved by UV light to produce even shorter analytical products, ready for mass spectrometric analysis. The use of "blockers" with specified properties in one type of the primers allows for even shorter analytical products.

Thus the procedure according to the invention consists of only one thermocy-cling and one washing process, followed by an easy, non-polluting cleavage procedure using a simple UV lamp delivering the final analytical DNA products for mass spectrometric analysis.

The photocleavable linkers have the following properties:
the linker can replace any nucleotide in a primer and maintains approximately the same distance between the neighboring nucleotides as the replaced nucleotide;
the linker does not hinder proper annealing of the primer to a complementary counter strand, whereby the primer can anneal to a complementary counter strand with an arbitrary nucleotide opposite the linker;
the linker does not hinder enzymatic elongation at the 3' end by the polymerase copying process if the linker is a few nucleotides away from the 3' end;
the linker stops the polymerase copying procedure if encountered in a template; and the linker is cleavable by UV light, thereby cleaving the DNA sequence.

As photocleavable linkers with the above mentioned additional features, building blocks from the o-nitrobenzyl derivatives class of compounds are particularly suitable. After converting the o-nitrobenzyl derivatives into DNA building blocks or analogues, these can be built into the primer at any position, replacing a regular nucleotide. Such onitrobenzyl derivatives do not interfere with annealing and only slightly lower the optimum annealing temperature during a DNA polymerase reaction. They are accepted by various polymerases as non-interfering the elongation at the 3' end if they are positioned a small number of nucleotides away from the 3' end. The synthesis and mechanism of photocleavable 1-(2-nitrophenyl)ethyl esters of various different phosphates and thiophosphates have already been examined in detail by Walker et al. (J. Am. Chem. Soc. 1988, 110, 7170–7177) and Ordoukhanian and Taylor (J. Am. Chem. Soc. 1995, 117, 9570–9571) but no application to mass spectrometry has been mentioned. It should be well understood that these linkers are by no means derivatives of nucleotides by just introducing other groups instead of the usual bases. The linker does not hinder the elongation of the primer at the 3' end by polymerases, whereby some polymerases require four nucleotides at the 3' end, others can start the copying process reliably with only three nucleotides between linker and 3' end. It is preferred to have the linker positioned as near to the 3' end as possible.

The blockers, built-in alternatively in one type of analytical primers, are defined by the following properties:

the blocker can replace a nucleotide in a primer;

the blocker does not hinder the annealing of the primer to a complementary counter strand;

the blocker does not hinder enzymatic elongation at the 3' end by the polymerase copying process even if the blocker holds the 3' position; and the blocker stops the polymerase copying procedure if encountered in a template.

As blockers, many different nucleotide derivatives can be used. There may be one blocker each for each of the four types of nucleotides; but this is not necessary. One of the easiest derivative usable as a blocker is the nucleoside thiophosphate which anneals properly, can be elongated by the polymerase, and stops the copying process if encountered in a template. It is favorable to use not just one nucleotide thiophosphate as a blocker, but two or three in a row to stop the polymerase copying process of a template reliably.

Other types of blockers are nucleotide derivatives where the base bonded to the sugar-phosphate backbone is replaced by a chemical group not correctly forming hydrogene bridges to the counter nucleotide, or not even forming hydrogen bridges at all. The blockers are preferredly positioned directly at the 3' end of the primer. In cases where the polymerase has difficulties to start elongation, it is possible to use a single regular nucleotide in the position at the 3' end, directly neighbored by the blocker nucleotide or nucleotides.

PCR amplification is thusly performed with a mixture of two pairs of primers: a first pair of "selection" primers controlling the PCR process and a second pair of "analytical" primers, whereby one of the analytical primers of the pair contains a linker, and the other analytical primer of the pair contains either a linker or a blocker. The two pairs of primers can be identical, except for the linker or blocker site, but preferredly the linker/blocker-containing analytical primer pair is "nested" in the PCR products generated by the pair of selection primers. The linker-containing analytical primers can be biotinylated at their 5' end for easy immobilization at a streptavidin-coated surface and washing. Of course any other affinity capture group can be used instead of the biotin, or a part of the sequence itself may be used for immobilization by hybridization.

Favorably, the primers contain the photocleavable linker about two to five nucleotides away from the 3' position. If the second primer of the pair contains a blocker, the blocker should be positioned at the 3' end, or at least in the position next to the 3' end.

The PCR amplification with the mixture of the two pairs of primers ends up with a high number of linker-containing DNA by-products which are already shortened beyond the mutation site because one of the earlier copying processes already had found a linker or blocker in the template to be copied (see FIGS. 2 and 3). If the linker-containing primers are biotinylated, then the final products can be immobilized at a surface covered with streptavidin, washed, and cleaved. The whole process produces the expected short DNA products, intermixed with products considerably longer because they still contain, at their 3' end, the complement of the full selection primer. These considerably longer DNA products may be washed away by size-specific adsorption, but this is not really necessary because they regularly do not disturb the MALDI or ESI analysis.

Using a pair of analytical primers, each of which contain linkers in the fifth position from the 3' position, the length of the short product will add up from four bases of one analytical primer, from four bases complementary to the other analytical primer, and from the length of the sequence between the primers. With only the mutation site between the primers, the length of the short product will amount to exactly 9 bases. If the linker can be placed nearer to the 3' end, the product can even be shorter. Samples from both strands are produced at the same time: the analytical result from one strand is corroborated by the analytical result of the other strand. If only one linker-containing analytical primer is biotinylated, only one strand is analysed.

Using a linker-containing primer and a blocker-containing primer as the analytical second pair of primers, the final product for mass spectrometric analysis is even still shorter: It may contain four bases from the linker-containing primer, plus the length of the strand between the analytical primers. With only the mutation site between the primers and with the blocker in the 3' position, the total length is only five bases: a pentamer is produced.

The PCR yield for the short products and the amount of longer chains in the final products depends very much on the ratio of linker/blocker-containing to linker/blockerfree primers in the mixture. If the primers of the analytical pair of primers both contain only linkers, and if the annealing process of all primers has the same probability, then the following relations hold true: The highest yield of wanted short DNA samples for analysis, obtained with the lowest number of thermo cycles, is achieved with a mixture of roughly 7% linker-containing analytical primers. A 1.5-fold larger amount of longer PCR products is intermixed, but these oligonucleotide will not be seen in the MALDI analysis. The PCR products, generated by the selection primers, amount to an 16-fold surplus. The surplus of PCR products can be diminished by larger percentages of analytical primers, but the ratio of analytical primers to PCR selection primers turns out to be not very critical. A compromise is a mixture of 10 to 20% of linker-containing analytical primers, but easily acceptable are ratios somewhere in the range from 3 to 30 percent.

It is one the special advantages of this invention that the photolytic cleavage does not introduce any additional pollutions as is the case with all chemical or enzymatic cleavage methods.

Following the PCR process, the analytical by-products are immobilized, e.g. by streptavidin-coated surfaces if the products are biotinylated, for a thorough washing. After washing, the linkers of the still immobilzed products are cleaved with a UV lamp. The free cleavage products now consist of the wanted short oligonucleotides of about five to eleven bases in length for an analytical pair of primers with only linkers, or with four to six bases in length for an analytical pair of primers with linkers and blockers, both intermixed with an slightly higher amount of products which contain the full primer length beyond the mutation site.

In case of MALDI ionization, the immobilization can directly take place on the sample support plate if biotinylated primers with linkers are used and the sample locations are coated with streptavidin. Such sample support plates can be coated with a highly hydrophobic coating, leaving only hundreds of small hydrophilic anchors for sample preparation. The anchors are coated with streptavidin, and the PCR solution is simply pipetted from a well of the microtitre plate used for PCR to such a sample anchor. Due to the hydrophibicity of the plate surrounding the anchor, the samples of different wells keep separated on the plate. The final analytical biotinylated oligonucleotides are immobilzed on the anchors, and the plate with hundreds of samples is thoroughly washed. After cleaving and drying, the free cleavage products are taken up by a pipetted drop of solvent with matrix substance for the MALDI process. After a second drying process, the support plate is ready for MALDI analysis in a time-of-flight mass spectrometer.

BRIEF DESCRIPTION OF THE DRAWINGS

FIG. 2 presents some initial, intermediate and final products of the PCR procedure when two primer pairs are used to perform the PCR, one pair (preferredly about 80 to 90%) without linkers and one pair with linkers. Oligomer (2a) is a part of the original DNA with nucleotides "N" containing the mutation site, designated with "P". Oligomer (2b) represents the counter strand; here the complementary nucleotides are named "M" and the complementary nucleotide of the mutation site is termed "Q". (2c) and (2d) represent the first primer pair with nucleosides "1" and "2" (the 3' end is marked by "–"), producing in the PCR process ample amounts of single-stranded DNA segments (2e) and (2f). The second pair (2g) and (2i) of analytical primers, with nucleotides "3" and "4" respectively, carrying linkers "L" near the 3' position and affinity groups "A" at the respective 5' positions. These primers deliver the products (2h) and (2j) if annealed to the products (2e) and (2f) and complementarily copied many times by the polymerase. If in following thermocycles the primers (2g) and (2i) of the second pair now anneal to the linker-containing products (2h) and (2j) as templates, the relatively short products (2k) and (2l) are produced because the copying process stops at the position of the linker in the template. After sufficient thermocycles of the PCR process, the linker-containing products (2h), (2j), (2k), and (2l) (plus some unused second primers) are extracted by affinity bonding the affinity group "A" to a suitable substrate. Washing and cleaving under a UV lamp produces the final products (2m), (2n), (2o), and (2p) which are analyzed by MALDI. The cleaving process leaves behind a phosphate group (designated by "+"), adding 80 atomic mass units after protonation. Since the longer products (2m) and (2o) cannot be seen because of their low sensitivity, only the mass signals of products (2n) and (2p) appear in the spectrum (possibly together with signals of the cleaved residual primers), showing the mass of the short products (2n) and (2p) (here 10 bases long), from which the nucleotide of the mutation site can be determined. Because strand and counter-strand of the original DNA are investigated at the same time, the determination of the mutation in the counter-strand forms a quality enhancement of the analysis procedure by automatic double-determination. If the primers (2g) and (2i) are not completely consumed durcing the PCR, these are extracted, too, and deliver some DNA quadrumer ions.

FIG. 3 presents a similar PCR procedure, using analytical primers with linkers "L" and analytical primers with blockers "B" as the analytical second pair of primers. Here, the final products consist of the longer products (3l) and the shorter products (3m), whereby the products (3m) are only five bases long. These are called pentamers.

DETAILED DESCRIPTION

Figure 1:
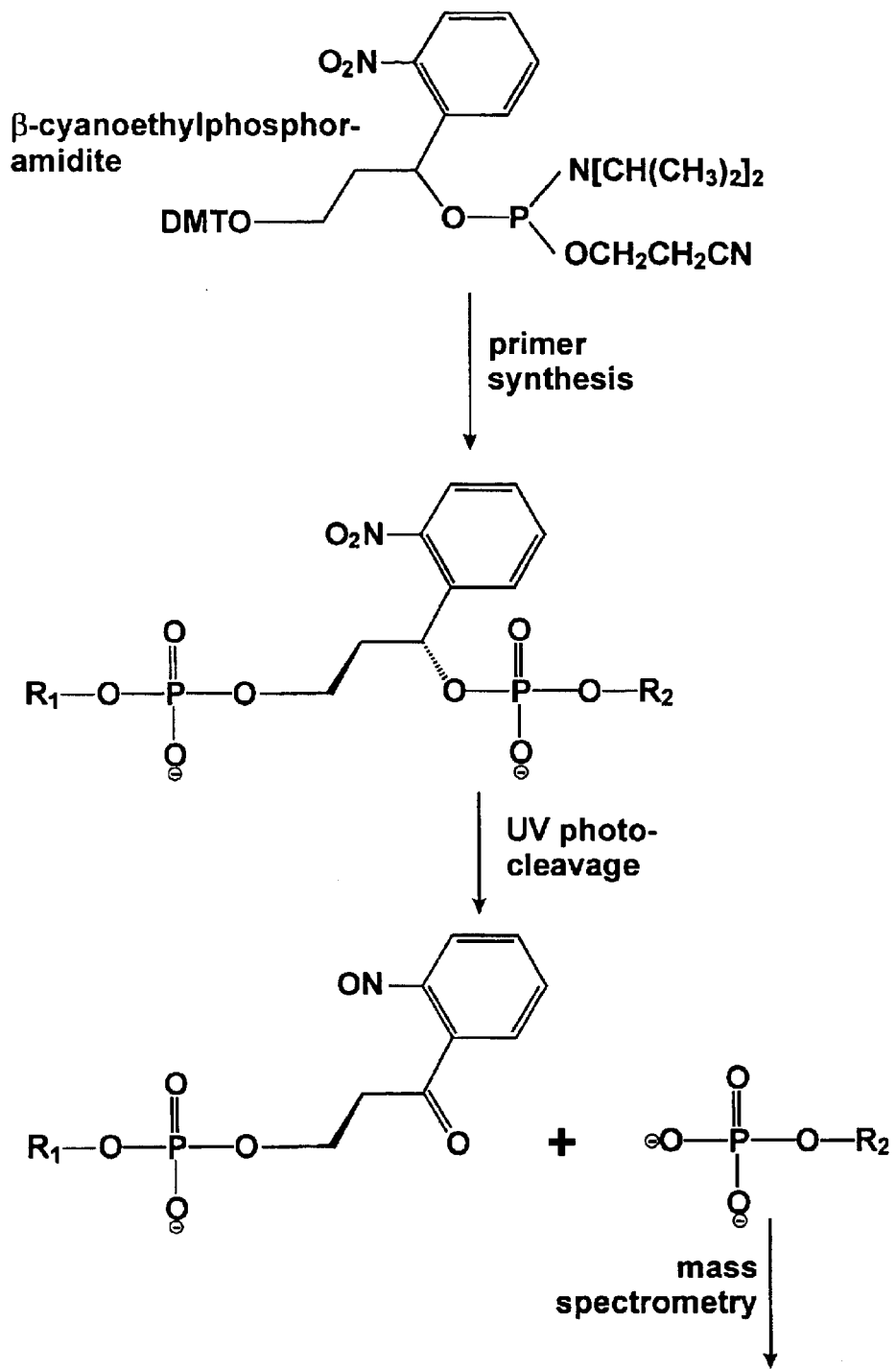
FIG. 1 shows the structure of the preferred linker. β-cyanoethylphosporamidite can be used to replace, during primer synthesis, a complete nucleotide. The linker bridges the neighboring nucleotides with the same distance as a true nucleotide, but does not contain any sugar (ribose). Hybridization of the linker-containing primer to the complementary master template is possible with any counter-nucleotide, whereby only a small decrease of the melting point is observed. $R_1$ and $R_2$ are two DNA sequences. Cleavage produces the $R_2$ sequence for mass spectrometric measurements, whereby the $R_2$ sequence is bound to a phosphate group with doubly negative anion character. After protonation of these two anions in the MALDI process, the phosphate group adds 80 atomic mass units to the weight of the protonated $R_2$ sequence.

The invention uses minor amounts of primers with photocleavable linkers, intermixed with a major amounts of primers without linkers, to produce short mutation-containing DNA sequences by enzymatic amplification procedures such as polymerase chain reactions (PCR). After this single amplification procedure, the linker-containing PCR by-products are extracted, washed and photolytically cleaved. Short oligonucleotides are produced which facilitate mass spectrometric analysis. Additionally to the use of linkers, some types of primers may contain blockers which stop the polymerase copying process to achieve even shorter oligonucleotides for analysis.

A first favorable embodiment of the invention consists in a PCR amplification which is performed with a mixture of a pair of normal PCR selection primers without linkers (2c) and (2d) of FIG. 2 and a pair of biotinylated, linker-containing analytical primers (2g) and (2i). Preferredly, the selection primer pair amounts to about 90 percent and the analytical primer pair to about 10 percent of all primer pairs. Both pairs of primers may have the same sequence, except for the linker; but in a preferred embodiment the linker-containing primer pair is "nested" inside the DNA product of the first selection primer pair, thus being annealed much nearer to the mutation site, as shown in FIG. 2. Most favorably, the analytical linker-containing primers are annealed directly next to the mutation site, as shown for primer (2*i*) in FIG. 2.

With the 90 percent selection primers (2*c*) and (2*d*) without linkers, the amplifying PCR procedure produces DNA-sequences of both strands embracing the mutation site, increasing the number of normal PCR products (2*e*) and (2*f*) in each thermocycle by a factor of 1.8. But beside this exponential PCR amplification by the linker-free primer pair (2*c*) and (2*d*), the 10 percent linker-containing primers (2*g*) and (2*i*) produce the sequences (2*h*) and (2*j*) as linker-containing by-products which cannot be amplified further in full length.

These by-products (2*h*) and (2*j*) can only be linearly amplified (up to the linker position) by selection linkers (2*c*) and (2*d*) respectively, getting products not shown in FIG. 2 for reasons of clarity. If it then happens that a linker-containing primer (2*g*) or (2*j*) anneals to these products or to the products (2*h*) or (2*j*) and is elongated by the polymerase, short products of the types (2*k*) or (2*l*) are produced; the further amplification of these products (2*k*) and (2*l*) is no longer possible. Thus the whole PCR procedure ends up with some amount of short biotinylated, linker-containing DNA by-products (2*k*) and (2*l*) which are already shortened to four or five bases at the other end of the mutation site.

The PCR amplification is usually performed in so-called thermocyclers, using microtitre plates with 384 wells each. The thermocyclers are controlled to perform the thermocycles automatically. The thermocycle consist of three phases each: melting (separation of strand and counterstrand) by a temperature in the 90s (degrees centigrade), annealing of the primers in the 50s, and polymerase complementary copying by prolongation of the primer at its 3' end in the 70s. After PCR thermocycling with about 30 to 40 cycles is complete, the PCR solutions from the wells in the microtitre plates are pipetted as small droplets to special sample locations on a sample support plate for the mass spectrometer. Preferredly, these sample support plates have the size of microtitre plates, and contain 384 small hydrophilic sample anchors on an otherwise hydrophobic plate surface. The anchors have diameters of about one millimeter, coated with streptavidin. The biotinylated products, consisting of the longer oligonucleotides (2*h*) and (2*j*), and the shorter oligonucleotides (2*k*) and (2*l*), are immobilized by affinity bonds between the biotin and the streptavidin.

The sample support plates are now thoroughly washed, and the linkers are cleaved by exposition to an UV lamp. The free cleavage products have the form of the oligonucleotides (2*m*), (2*n*), (2*o*), and (2*p*), with the addition of a phosphate group each stemming from the linkers. These free analyte products are taken up by a solvent drop containing the matrix substance for the MALDI process. Drying grows small matrix crystals with built-in analyte molecules, ready for MALDI analysis. During the MALDI process in the ion source of the mass spectrometer, the short products (2*n*) and (2*p*) which amount to roughly 40 percent of the free cleavage products, are preferredly ionized and analyzed.

The free products (2*n*) and (2*p*) consist of four bases each from the primer's 3' end (or the complement of it), and one to three bases including the mutation site. An optimum length for the short product is about nine to eleven bases.

In the preferred embodiment with both linker-containing primers carrying the biotin group, both strands are analysed automatically for the mutation, increasing the accuracy of the analytical result by confirmation. If only one linker-containing primer of the analytical primer pair is biotinylated, only the mutation in one strand is analysed.

The PCR yield and the amount of longer chains (2*m*) and (2*o*) in the final product mixture depends weakly on the ratio of linker-containing and linker-free primers in the mixture. If the probability for annealing is equal for all four primers, the highest yield of short DNA samples for analysis, obtained with the lowest number of thermocycles, is achieved when a mixture with roughly 7% of linker-containing primers is used (exactly 6.9%). This is the result of a mathematical simulation assuming equal hybridization rates for both primer pairs. But in this case, a 1.5-fold surplus of longer PCR products (2*m*) and (2*o*) is intermixed with the short chains (2*n*) and (2*p*). With higher percentages of linker-containing primers (2*g*) and (2*i*) is used, the ratio of the short products (2*n*) and (2*p*) to the long products (2*m*) and (2*o*) can be somewhat reduced, but the total yield for these products is somewhat lower and requires more temperature cycles. With a higher percentage of linker-containing primers, the PCR yield is reduced. A compromise is a mixture of 10 to 20% of linker-containing primers. The long products (2*m*) and (2*o*), respectively, cannot be seen in MALDI mass spectrometry because of their much lower sensitivity. In simulations, a production factor of about $10^9$ for the short products (2*n*) and (2*p*) is achieved in about 35 temperature cycles with these mixture ratios.

The immobilization by biotin-streptavidin bonding can easily be replaced by other types of bonding well known to the specialists in the field. A special type of immobilization can be achieved by use of seize-specific adsorption, controlled by buffers. Magnetic beads and corresponding buffers for this purpose are on the market (e.g. Genopure™ from Bruker Saxonia Analytik GmbH, Leipzig).

As indicated above, the linker-containing primers (2*g*) and (2*i*) must not be identical with the linker-free primers (2*c*) and (2*d*) in the sequence of bases except the linker. They even can be considerably shorter. Linker-containing primers may be used which hybridize much nearer to the mutation site, on one or both sides. This allows for the selection of non-interfering, non-folding PCR selection primers for the exponential amplification process, and for a pair of nested, short primers containing the linkers and producing the final short products.

There are of course several variaties to this process. To reduce the number of thermocycles in order not to fade out the effectiveness of the polymerase which has a halflife of only about 20 cycles, the well-known "touch-down PCR process" may be used: If the analytical primers are shorter than the selection primers and therefore show a lower optimum annealing temperature, the first PCR cycles may be performed with higher annealing temperature hindering the analytical primers to anneal. Normal PCR amplification rates with the selection primers are thus achieved. Only in later cycles, the annealing tempertures are lowered to hybridize the analytical primers with linkers (and with blockers, see next paragraph). The percentage of the analytical primers may be chosen considerably higher with this touchdown process, and sufficient amounts of final by-products can be generated with a lower number of cycles. The percentage of analytical primers can be in the range of 20 to 50 percent, but it should be considered that the analytical primers should be almost completely consumed in the PCR process because the non-used primers are contained in the final products for mass spectrometric measurements (see below). Commercially available thermocyclers can be programmed to perform this touch-down process automatically.

A second preferred embodiment with "blockers" produces even shorter oligonucleotides for mutation analyses by mass spectrometry. The blockers are used in one type (3g) of the analytical primer pair, whereas the other primer (3i) of the pair contains a linker. The original strands (3a) and (3b), some intermediate, and the final products (3l) and (3m) of this procedure are presented in FIG. 3. This procedure produces, after cleavage, extremely short oligonucleotides (3m) of only four to six bases in length, best suited for mass spectrometric measurements.

In detail, parts of the original DNA strands (3a) and (3b) are exponentially amplified by the selection primers (3c) and (3d) to the products (3e) and (3f). The blocker-containing analytical primer (3g) produces the by-product (3h) containing a blocker. If the linker-containing analytical primer (3i) anneals to the by-product (3h), the polymerase produces the linker-containing by-product (3k). This product can be immobilized because of its affinity group "A" to a suitable substrate, washed, and cleaved, whereby the free oligonucleotide (3m) is formed; the product (3m) consists of five bases only (plus a phosphate group from the linker) and contains the information which base was built into the mutation site of the original strand (3a).

Figure 4:
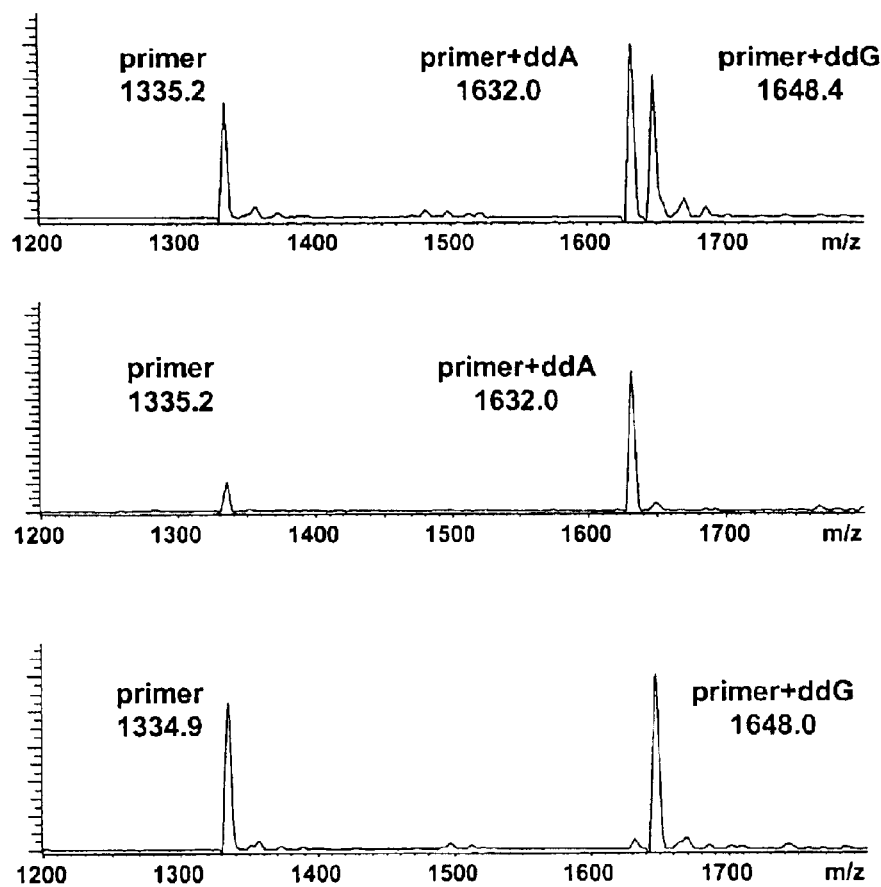
FIG. 4 exhibits three mass spectra of DNA pentamers, here produced from samples obtained by the extension of primers with linkers as shown in FIG. 1, and subsequent cleavage, therefore carrying one additional phosphate group (80 atomic mass units after protonation). The SNP is named PAI1. The upper spectrum shows the heterozygous case, the two lower spectra present the two homozygous cases. In all three spectra, the leftovers of the non-elongated extension primers are visible as DNA quadrumer ions; these may serve as easy mass references.

If the biotinylated primers (3i) are not completly consumed by the PCR process, these primers are also extracted, washed and cleaved together with the oligomers (3j) and (3k), forming some tetramer ions. These tetramer ions have exactly known masses and may therefore serve as mass references for the mass determination process. FIG. 4 shows this situation with linker-containing DNA products cleaved delivering pentamers, and leftover linker-containing primers cleaved delivering tetramers, which then serve as mass references. The measurements of FIG. 4 are based upon exactly the linkers shown in FIG. 1.

As blockers, derivatives of nucleotides can be used which do hinder the copying process of the polymerase if encountered in a template. The elongation process by the polymerase is controlled by the hydrogen bonds between the nucleotide in the template and the building block to be built into the DNA chain being elongated. It is well-known, that the hybridization or annealing process between strand and counterstrand forms either two or three well-defined hydrogen bridges between pairs of nucleotides. If now a nucleotide derivative contains, instead of one of the four bases, a group forming greatly incorrect hydrogen bridges, or only one or even no hydrogen bond at all, it will form a blocker. The blocker-containing primer will still anneal, and the blocker can even be elongated if positioned at the 3' end of the primer. But if encountered in the template, the blocker nucleotide derivative does not show the right hydrogene bridge motive to find a counter nucleotide; the copying process will be stopped. The biochemist in the field will be able, with the information given here, to find hundreds of different types of derivatives of nucleotides which can be used as blockers.

Another type of blocker is obtained if the backbone is derivatized to stop the copying process, e.g. by a phosphor thioate group instead of the normal phosphate group. This group forms a somewhat weak blocker, and needs, for some types of polymerase, to be used in double or even triple positions to reliably stop the copying process.

The blocker-containing primers must not be applied in exactly the same amount as the linker-containing primers. It may be favorable to use much more blocker-containing primers than linker-containing primers.

The touch-down process with a PCR process starting at higher annealing temperatures first and then come down to annealing temperatures for the linker and blocker containing analytical primers can surely applied here, too. Also extraction processes with adsorptive magnetic beads (e.g. GenoPure™) instead of affinity groups bonded to the analytical linker-containing primers, can be used here.

The process outlined here for the preparation of analytical oligonucleotides of short length for the investigation of mutation sites by mass spectrometry, exposes several advantages. Firstly, only a single thermocycling phase has to be applied, saving time and effort. Secondly, the expensive thermosequenase as polymerase for the primer extension is no longer necessary, the inexpensive tac-polymerase may be used as usual for this amplification. Thirdly, the washing process by bonding the products to a substrate and subsequently cleaving is extremely simple.

The PCR process of generating products suitable for mass spectrometric mutation measurements can also be multiplexed to deliver more than one mutation-dependent product in the same process. The multiplexing process for PCR is well-known to the specialist in the field.

What is claimed is:

1. Method for mass-spectrometric analysis of a known mutation site in DNA, comprising the following steps:
   (a) amplifying a DNA sequence by polymerase chain reaction, using a first pair and a second pair of primers wherein the second of primers encloses the mutation site and is nested within the DNA range of the first pair of primers, and wherein at least one of the primers of the second pair contains photocleavable linkers,
   (b) extracting linker-containing amplification products resulting from the amplification,
   (c) cleaving the extracted linker-containing amplification products, and
   (d) analyzing the cleavage products by mass spectrometry.

2. Method as in claim 1, wherein one of the primers of the second pair contains photocleavable linkers, and wherein the other primer of the second pair contains polymerase chain reaction blockers.

3. Method as in claim 1, wherein the linkers are located in firm positions 3 to 7 bases from the 3' position of the primers.

4. Method as in claim 1, wherein the linker stems from the class of chemical compounds known as o-nitrobenzyl derivatives.

5. Method as in claim 4, wherein the substance to synthesize the linker during primer synthesis is β-cyanoethylphosphoramidite.

6. Method as in claim 1, wherein at least one of the linker-containing primers contains also an affinity group, and wherein affinity bonding to a substrate is used to extract, in step (b), the linker-containing primers carrying the affinity groups.

7. Method as in claim 2, wherein the blocker is located in the 3' position or in the position next to the 3' position.

8. Method as in claim 7, wherein the blocker is a nucleaside thiophosphate.

9. Method as in claim 7, wherein the blocker is a nucleotide derivative not matching the hydrogen bond sites of any of the four bases.

10. Method as in claim 1, wherein the ratio of the second pair of primers to the first pair of primers is within the range of 3 and 30 percent.

11. Method as in claim 10, wherein the ratio of the second pair of primers to the first pair of primers is within the range of 7 and 20 percent.

12. Method as in claim 1, wherein a multiplexing polymerase chain reaction with information about more than one mutation site is used with at least one first pair of primers and at least two second pairs of primers.

13. Method as in claim 1, wherein the polymerase chain reaction amplification starts with higher annealing temperatures in the first thermocycles, and continues later with lower annealing temperatures.

14. Method as in claim 13, wherein a ratio of the second pair of primers to the first pair of primers is within the range of 20 to 50 percent.

* * * * *